(12) United States Patent
Basoglu et al.

(10) Patent No.: US 8,303,655 B2
(45) Date of Patent: *Nov. 6, 2012

(54) OCULAR IMPLANT IRIS DIAPHRAGM

(75) Inventors: Ayhan Basoglu, Pittsfield, MA (US); Richard Albert Vanegas, New York, NY (US)

(73) Assignee: Stellar Devices LLC, New York, NY (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/041,714

(22) Filed: Mar. 7, 2011

(65) Prior Publication Data

US 2011/0264210 A1 Oct. 27, 2011

Related U.S. Application Data

(63) Continuation of application No. PCT/US2011/026025, filed on Feb. 24, 2011, which is a continuation-in-part of application No. 12/767,527, filed on Apr. 26, 2010, now Pat. No. 8,197,540.

(51) Int. Cl.
*A61F 2/14* (2006.01)
(52) U.S. Cl. ........................................................ 623/4.1
(58) Field of Classification Search .................. 623/6.36, 623/4.1, 6.14, 6.38–6.41, 6.43–6.47, 6.49
See application file for complete search history.

(56) References Cited

U.S. PATENT DOCUMENTS

| 3,866,249 A * | 2/1975 | Flom ............................ 623/6.12 |
| 6,079,417 A | 6/2000 | Fugo |
| 6,280,469 B1 | 8/2001 | Terry et al. |
| 7,025,781 B2 | 4/2006 | Kahn |
| 2004/0153148 A1 * | 8/2004 | Kahn .............................. 623/4.1 |
| 2005/0015143 A1 * | 1/2005 | Willis et al. .................. 623/6.36 |
| 2006/0253196 A1 * | 11/2006 | Woods ......................... 623/6.13 |
| 2006/0271184 A1 * | 11/2006 | Silvestrini .................... 623/5.16 |
| 2007/0088432 A1 | 4/2007 | Solovay et al. |
| 2007/0162114 A1 * | 7/2007 | Hermeking .................... 623/4.1 |

* cited by examiner

*Primary Examiner* — David H Willse
*Assistant Examiner* — Tiffany Shipmon
(74) *Attorney, Agent, or Firm* — Louis Ventre, Jr.

(57) ABSTRACT

An ocular implant alters iris color for medical and cosmetic purposes and is made of an inert, nontoxic, foldable and preferably permeable to fluid flow material. It is an annular non-planar structure that fits over the iris yet leaves the natural lens uncovered and extends approximately to the iridocorneal angle. Two different kinds of arc sections of a non-uniform thickness make up the structure: passage arc sections and support arc sections. The passage arc sections permit humor aqueous flow under the implant. The support arc sections make contact with the iris and provide the necessary support for the passage arc sections. Auricles extend from the support arc sections and are configured to hold the implant in place by engaging the eye at the iridocorneal angle. The implant may include an artificial lens, a limbal ring, and various means to anchor for the artificial lens.

6 Claims, 8 Drawing Sheets

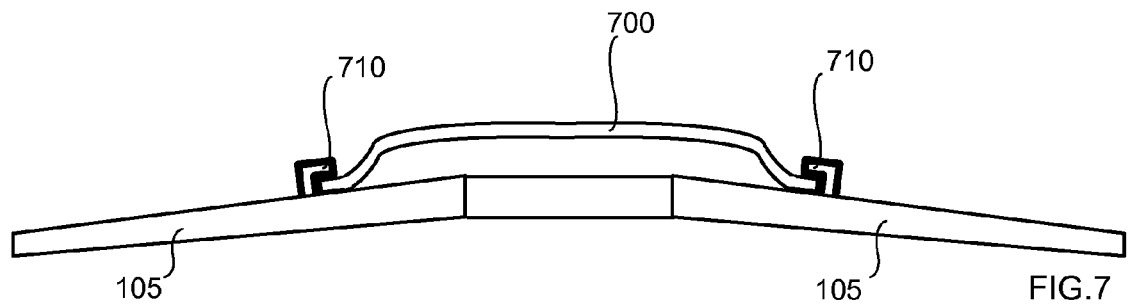
FIG.7
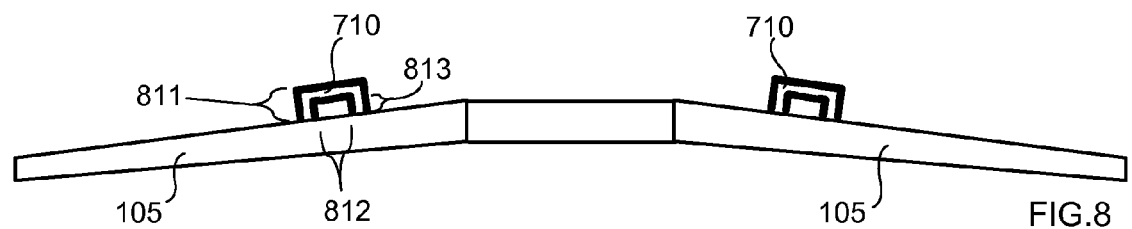
FIG.8
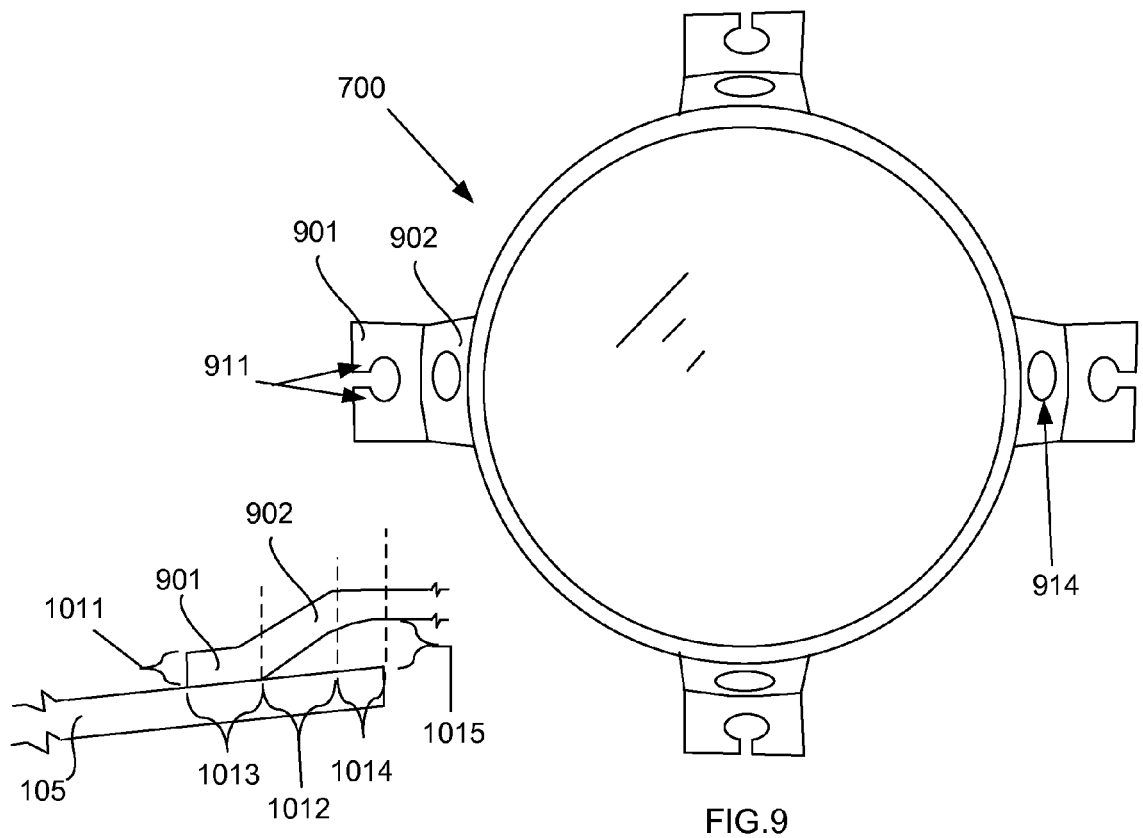
FIG.9
FIG.10

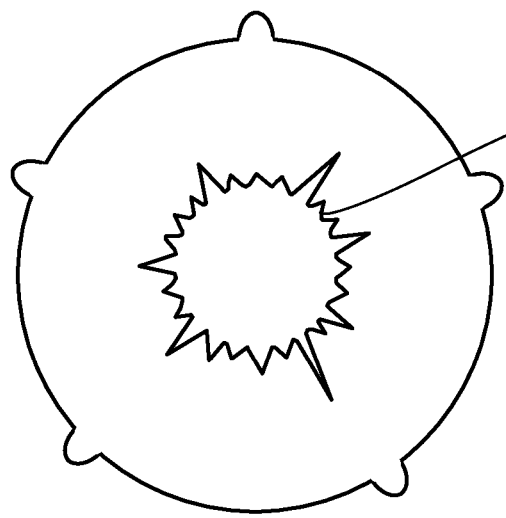
FIG.14
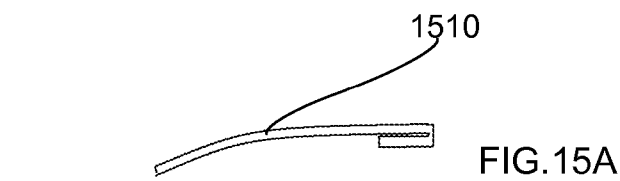
FIG.15A
FIG.15B
FIG.15C
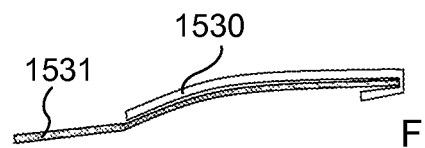
FIG.15D
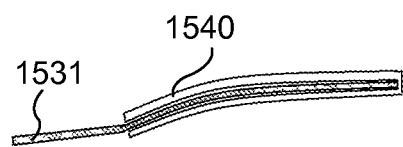
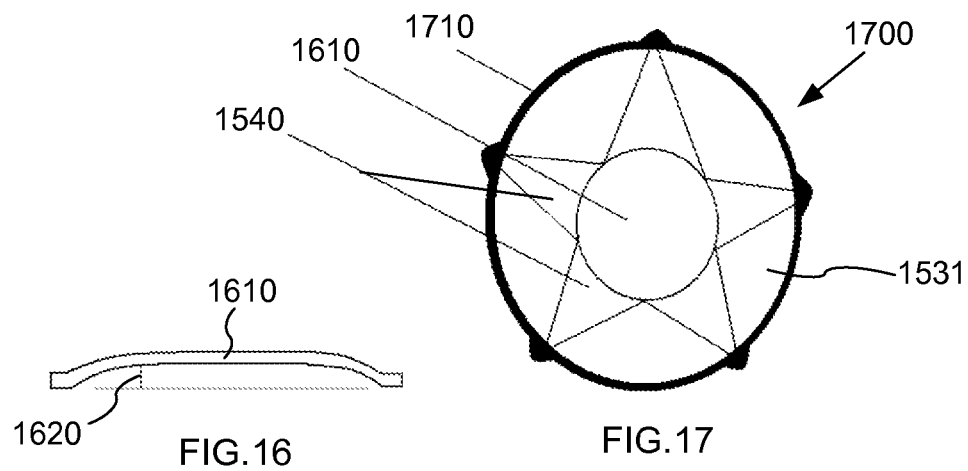
FIG.16
FIG.17

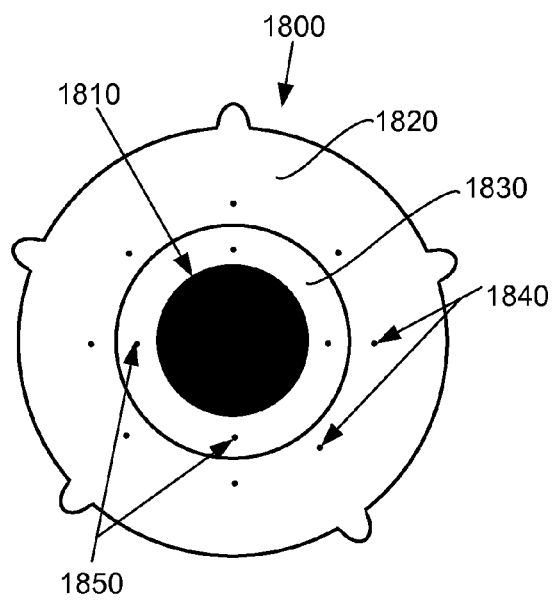
FIG.18
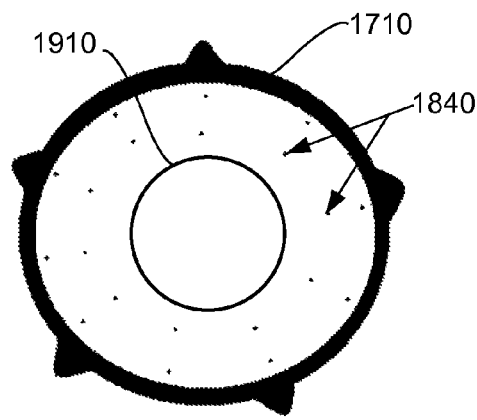
FIG.19
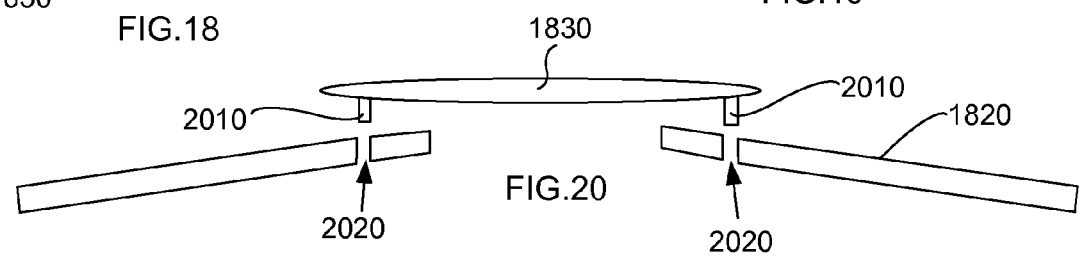
FIG.20
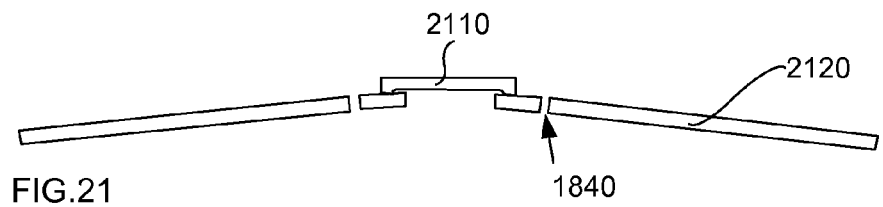
FIG.21
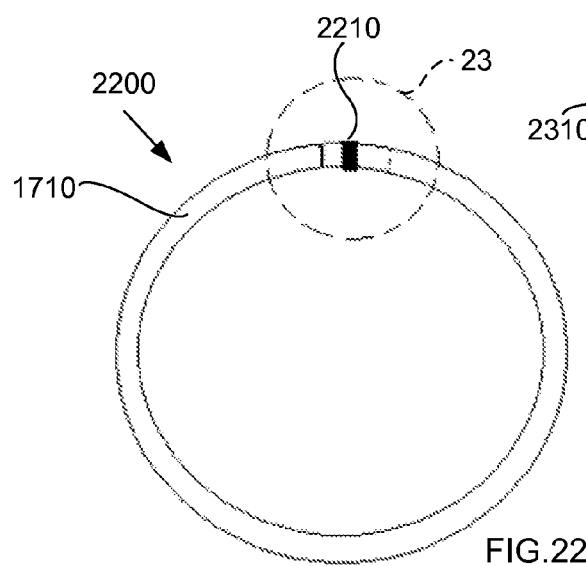
FIG.22
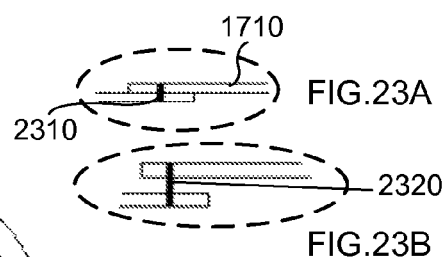
FIG.23A
FIG.23B

OCULAR IMPLANT IRIS DIAPHRAGM

CROSS-REFERENCE TO RELATED APPLICATIONS

This application is a continuation of International Application No. PCT/US2011/026025, filed 24 Feb. 2011, which claims the benefit of U.S. patent application Ser. No. 12/767,527, filed 26 Apr. 2010, which are hereby incorporated by reference herein.

TECHNICAL FIELD

In the field of eye prosthesis, an ocular implant is in the form of an iris diaphragm adapted to permanently cover the pigmented tissue in front of the crystalline lens of the natural living organ capable of vision or light sensitivity.

BACKGROUND ART

There are numerous medical conditions where changing the color of the eyes is a suitable treatment. These include fixing heterochromia, protecting the eyes of the albinos from the harmful effects of the sunlight, covering up the defects of the iris such as coloboma, severe iris atrophies, and iridoschisis. There is also a need for eye color changes for cosmetic purposes.

An opening in the front of a human eye is called a pupil and it permits entry of light into the eyeball, through the lens of the eye and onto the retina. The size of the pupil is controlled by an iris. The iris has a natural color which is considered the color of the eye.

The state of existing technology in eye implantation of iris overlays in the anterior chamber is disclosed in U.S. Pat. No. 7,025,781 ('781 patent) for an artificial soft iris diaphragm implant. The '781 patent diaphragm is a smooth, flexible and foldable material forming a main portion. In contrast, there is no corresponding main portion in the present implant because it is structured with arc sections that are non-planar, arranged in a non-smooth pattern that enables specific and essential improvements to the performance of the implant.

The '781 patent teaches implants that contain "flap portions" that are "integrally formed with the main portion to provide the diaphragm with a unitary construction." The "main portion" in the '781 patent is "smooth." In contrast, there is no main portion in the present invention because the implant comprises multiple non-uniform and non-planar components in the thicker support arc sections and thinner passage arc sections. These sections differ significantly in thickness and purpose, and define a structure that is non-planar, non-smooth, and non-uniform.

A functional significance of the arc sections of the present invention is that they significantly diminish the contact surface between the implant and the iris, thereby diminishing the postoperative inflammation related to friction between the implant and the iris, reducing the possibility of glaucoma and also preventing the desquamation of the pigment cells into the anterior chamber.

Unlike the '781 patent, only the much thicker support arc sections of the present invention have auricles that extend from the support arc sections of the diaphragm. These auricles that extend from the support arc sections are not an integral part of the passage arc sections of the diaphragm. Unlike the '781 patent, the present invention provides no uniformity between the support arc sections and the passage arc sections.

SUMMARY OF INVENTION

An implant is disclosed for an eye to alter iris color for medical and cosmetic purposes. The implant is made of a material that is inert, nontoxic, foldable and preferably permeable to fluid flow. The material configured to define an annular non-planar structure that fits over the iris yet leaves the natural lens uncovered. The implant extends approximately to the iridocorneal angle. The annular non-planar structure an assembly of two different kinds of arc sections of a non-uniform thickness. These kinds are passage arc sections and support arc sections. The passage arc sections define passages for humor aqueous flow under the implant because they are supported in a position at a distance above the iris. The support arc sections make contact with the iris and provide the necessary support for the passage arc sections. Auricles extend from the support arc sections and are configured to hold the implant in place by engaging the eye at the iridocorneal angle.

The implant may include an artificial lens and with that embodiment, preferably four spurs rise from support arc section and provide an anchor for the artificial lens. The spur may be in any form but two examples include an open angle shape and a closed loop shape. The artificial lens preferably has four haptics or attachment structures to hold the artificial lens in position and to elevate the artificial lens off the top surface of the arc sections. The haptics may be a closed hole to fit over the spur or a sliced hole or pincer to snap in place around a closed-loop-shape spur.

Technical Problem

Existing implants can create significant medical problems due at least in part to interference with humor aqueous flow and excessive contact between the implant and the iris pigment cells. Post implant problems such as ocular hypertension, iritis, corneal oedema, cataract, glaucoma and infection can lead to vision loss. Problems reported include hyphaema, uncontrolled intraocular pressure, severe endothelial cell loss, bullous keratopathy and anterior uveitis, permanent damage to the trabecular meshwork and corneal endothelium can persist.

Some existing iris prosthesis implants may only be implanted into the posterior chamber, not the anterior chamber in front of the iris or iris remnant because of the danger of damage to the corneal endothelium as well as the danger of severe intraocular pressure increase.

Existing techniques for implantation of aniridia lenses require that the crystalline lens of the patient be removed even if the patient doesn't have a cataract. In other words, the patient has to undergo cataract surgery.

Solution to Problem

An ocular implant within the anterior chamber that covers the iris with a minimal mass, yet permits humor aqueous flow and that has minimal contact with the surface of the iris.

Advantageous Effects of Invention

The ocular implant is useful in treating heterochromia, protecting the eyes of an albino from the harmful effects of the sunlight, covering defects of the iris such as coloboma, severe iris atrophies, and iridoschisis, and for simple cosmetic purposes.

The unique arc sections of ocular implant define passages above the iris which can cut the contact surface with the iris in half while enabling fluid flow of the humor aqueous. The configuration of these arc sections diminishes postoperative inflammation related to friction between the implant and the iris. By diminishing the frictional surface, the implant minimizes the desquamation of the pigment cells into the anterior chamber, which can later cause obstruction in the trabecular meshwork and increased intraocular pressure and resulting glaucoma. These arc sections also avoid the problems inherent in the prior art of obstructing drainage of the humor aqueous from the eye through the trabecular meshwork via the anterior chamber. Thus, the invention decreases the probability of secondary glaucoma.

A primary embodiment of the ocular implant is for treatment when corrective artificial lenses are not needed or desired. This embodiment is non-refractive and is, thus, a solution to medical treatments requiring an unobstructed visual axis using the eye's natural lens. The most prominent advantage of invention over the prior art involving aniridia lenses, is that human crystalline lens is not removed. So, the invention enables subsequent removal of the refractive part for whatever reason.

The ocular implant is supported in the anterior chamber, and is structured to enable humor aqueous flow under the ocular implant.

The ocular implant is much thinner than other implants, which effectively means that reducing the mass of the implant also reduces the potential for adverse effects from adding artificial components to the eye. The ocular implant is held in place at the iridocorneal angle without causing great pressure to the angle structures.

While the ocular implant is designed to be a permanent medical treatment, it can be removed if desired.

The ocular implant may include a lens and the advantages of phakic intraocular lens include no thinning of the cornea and the ability to remove the implanted lens if problems arise or a change in the power of the lens is required. And because the eye's natural lens is left intact, there is no loss in a patient's ability to change focus (if they are under age 40 and do not have presbyopia). This new refractive combination is especially better than existing treatments for astigmatism and is easier to put into the eye. The additional holes for flow of aqueous humor solve the problems of complications due to flow blockage.

The refractive lens of the implant can be made with an ultraviolet protected tint and so can be used to treat and reduce the sensitivity in the eyes of albinos. An albino does not have melanin pigment even in their retina pigment cell layers.

BRIEF DESCRIPTION OF DRAWINGS

The drawings illustrate preferred embodiments of the ocular implant according to the invention and the reference numbers in the drawings are used consistently throughout. New reference numbers in FIG. 2 are given the 200 series numbers. Similarly, new reference numbers in each succeeding drawing are given a corresponding series number beginning with the figure number.

FIG. 7 is a side elevation view of the ocular implant with an artificial lens.

FIG. 8 is a sectional side-elevation view of the ocular implant showing a closed-loop-shape spur used to anchor an optional artificial lens to the ocular implant.

FIG. 9 is a plan view of a second lens with a haptic including a pincer used to anchor an optional artificial lens to the ocular implant.

FIG. 10 is a side elevation view of a portion of the second lens atop a portion of the ocular implant.

FIG. 14 is a plan view of an implant with a corrugated iris opening.

FIG. 15A is a sectional view of a hairclip device for supporting an artificial lens, the hairclip device having an end folded down to hold the main body of the implant underneath the hairclip device.

FIG. 15B is a sectional view of a hairclip device with an end folded up to hold the main body above the hairclip device.

FIG. 15C is a sectional view of a hairclip device with an end angled down to wedge the main body underneath the hairclip device.

FIG. 15D is a sectional view of a hairclip device with a slotted configuration to hold the main body in the slot.

FIG. 16 is a sectional view of a fifth artificial refractive lens showing a vault height.

FIG. 17 is a plan view of a first alternative implant having an artificial lens with hairclip devices to support the lens above the surface of the eye.

FIG. 18 is a plan view of a second alternative implant having an artificial lens with protrusions for fitting into holes in the main body of the implant.

FIG. 19 is a plan view of a third artificial implant with a peripheric ring and an artificial refractive lens.

FIG. 20 is an elevation view of the second alternative implant showing the protrusions and mating holes in the main body.

FIG. 21 is an elevation view of an implant with a glued artificial lens.

FIG. 22 is a plan view of an alternative peripheric ring with a connector.

FIG. 23A is a plan view showing a magnified portion of the peripheric ring with sealed pin joint.

FIG. 23B is a plan view showing a magnified portion of the peripheric ring with separated pin joint.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Figure 1:
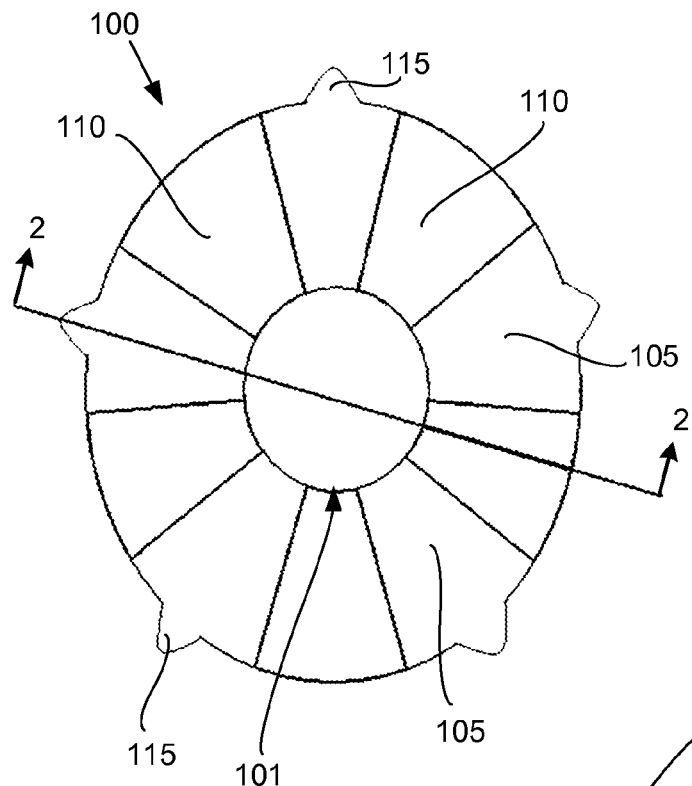
FIG. 1 is a plan view of the ocular implant surface that will face the iris when implanted in the eye.
Figure 3:
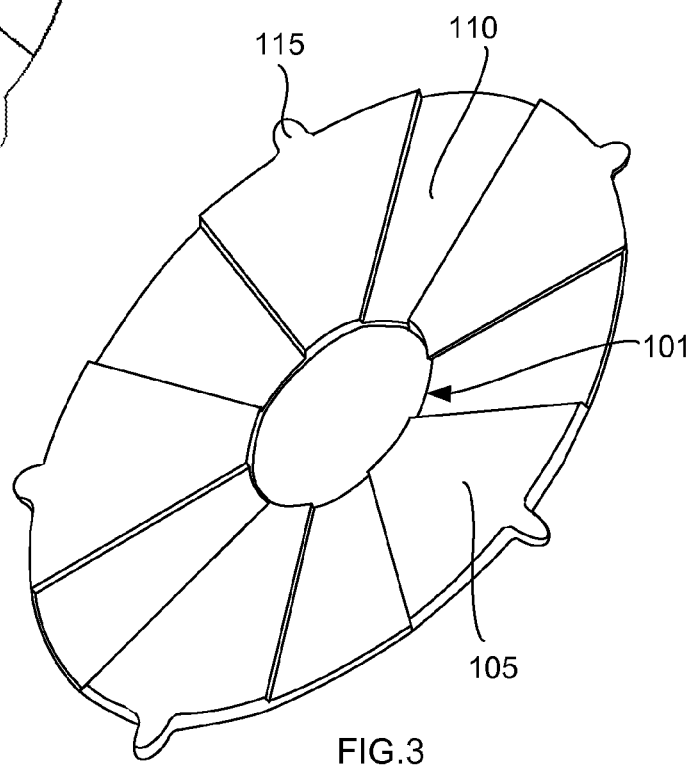
FIG. 3 is a perspective of the ocular implant surface shown in FIG. 1.
Figure 2:
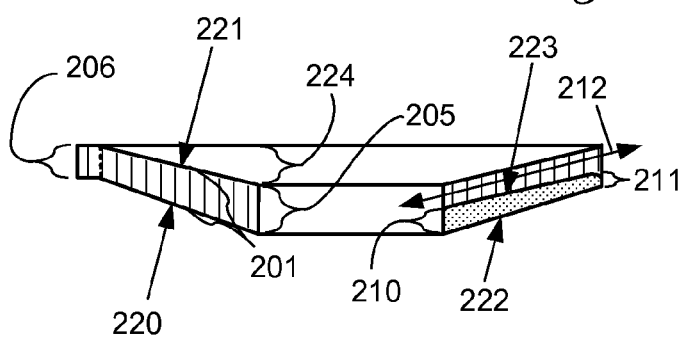
FIG. 2 is an elevation view of the ocular implant at section 2-2 in FIG. 1.
Figure 4:
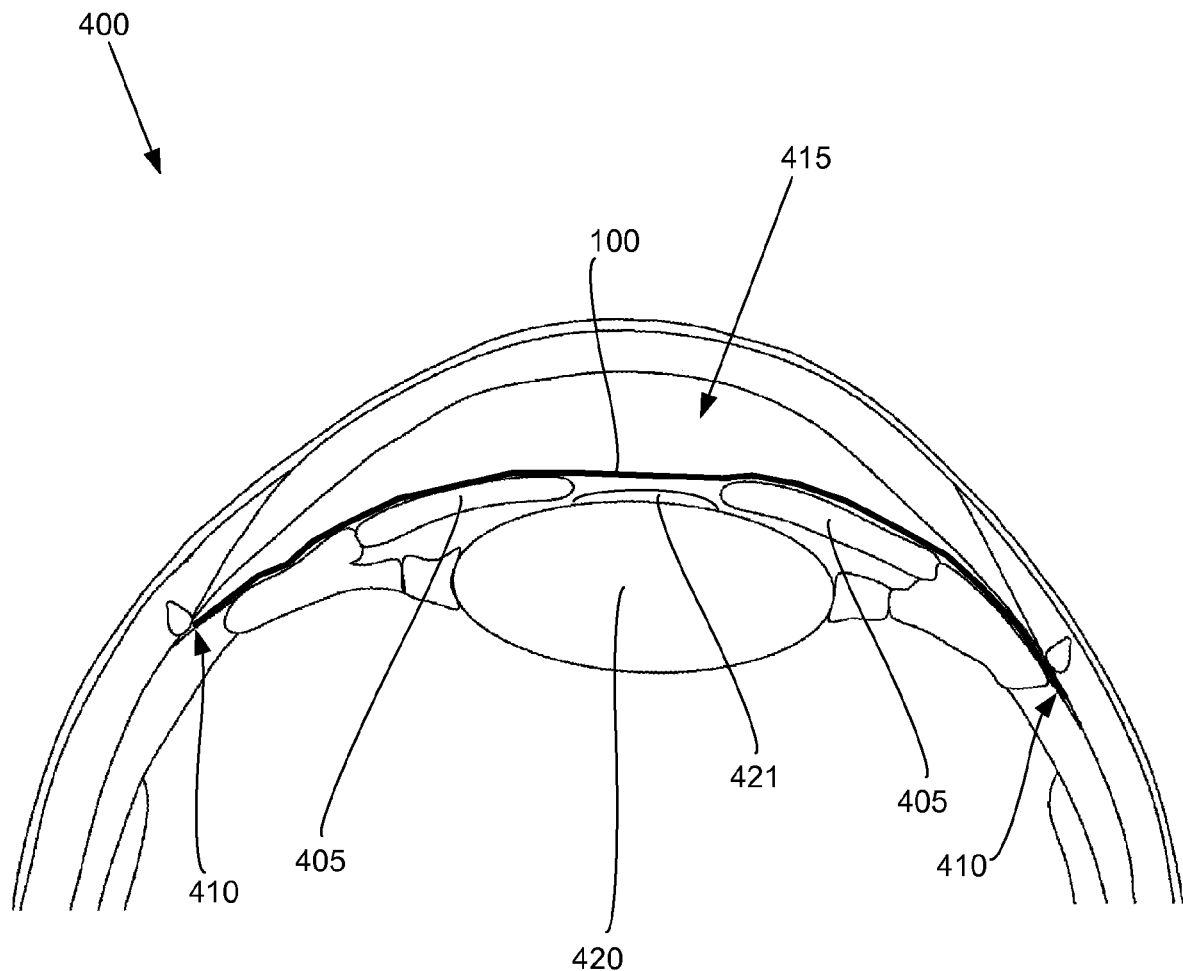
FIG. 4 is an elevation of a vertically-oriented eye showing the location of the ocular implant within the eye.

FIGS. 1-3 show a preferred embodiment of the ocular implant in several views and FIG. 4 shows after implantation within an eye. The preferred embodiment is an implant (100) for an eye (400), the eye (400) comprising an anterior chamber (415), an iridocorneal angle (410), a natural lens (420), and an iris (405), and pupil opening (101). The implant (100) is configured to extend over the iris (405) within the anterior chamber (415) to alter iris (405) color for medical and cosmetic purposes. Both sides of the implant can be colored, but preferably only the top surface, that is the surface not in contact with the iris (405), is colored. Varied iris openings are possible, for example, FIG. 14 illustrates a corrugated iris hole (1410).

The implant (100) includes a material that is inert, nontoxic and foldable, which is configured to define an annular non-planar structure, also referred to herein as the main body of the implant (100). This material is preferably a hydrophilic acrylic, silicone or plastic with elasticity, flexibility and biocompatible. Heparin surface modification of intraocular implants has been shown to diminish postoperative inflammation to enhance biocompatibility. Accordingly, heparin surface modification may be performed in order to augment the biocompatibility of the implant.

Figure 13:
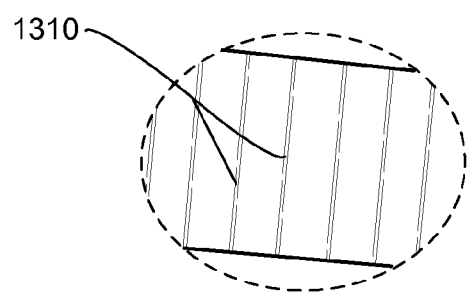
FIG. 13 is a magnification showing micro-holes through the ocular implant.

The material is optionally configured to define a plurality of microscopic holes to render the material permeable to fluid within the eye (400). FIG. 13 is a magnification of the portion (13) of the ocular implant shown in FIG. 11 to illustrate the microscopic holes (1310) that permit aqueous humor flow through the ocular implant. These microscopic holes (1310) are throughout the ocular implant in both support arc sections (105) and passage arc sections (110).

The annular non-planar structure is configured to leave the natural lens (420) uncovered and is further configured to extend approximately to the iridocorneal angle (410) (also known as the iridial angle) when implanted in the eye (400) atop the iris (405). The annular non-planar structure, thus, includes, in preferred embodiments, a central opening corresponding to the pupil (421) of the human eye. For human eyes, the central opening is usually between 3 to 4 millimeters in diameter, preferably about 3.5 millimeters in diameter.

The annular non-planar structure includes a plurality of arc sections (105 and 110) of a non-uniform thickness (201) diminishing from the central opening to the periphery, that is, in a radial direction away from the central opening. The arc sections include support arc sections (105) and passage arc sections (110).

Each arc section comprises a top surface and a bottom surface. Thus, there is a support-arc-section top-surface (220); a support-arc-section bottom-surface (221); a passage-arc-section top-surface (222); and a passage-arc-section bottom-surface (223). The top surface designation is generally that which is away from the iris (405) when implanted in the eye (400). When implanted, the distance or vault height (224) from the surface of the iris (405) at the edge of the central opening to the support-arc-section bottom-surface (221) is typically about 0.3 to 0.5 millimeters. With this vault height (223), it has an anatomic compatibility with the iris (405) in the anterior chamber (415) of the eye (400).

The arc sections are configured, when implanted in the eye (400) atop the iris (405), to define passages (212), indicated by the double arrow, for humor aqueous flow under the implant (100) formed by passage arc sections (110) that sit a distance above the iris (405). The passage arc sections (110) uniquely enable flow of the humour aqueous between the pupil and the trabecular meshwork at the iridocorneal angle.

The arc sections are configured, when implanted in the eye (400) atop the iris (405), to define a support structure for the passages (212) formed by support arc sections (105) that are in contact with the iris (405). Such contact with the iris (405) is typically limited to the area near the periphery of the support arc sections (105) at the iridocorneal angle (410). When implanted, the support-arc-section bottom-surface (221) and the passage-arc-section bottom-surface face the iris (405).

Each of the support arc sections (105) is a thick part tapering outwardly, that is, towards the periphery. The support-arc-section maximal thickness (205) is preferably about 0.16 to 0.18 millimeters thick near the central opening. The support-arc-section minimal thickness (206) is preferably about 0.12 to 0.14 millimeters thick at the periphery.

Each of the passage arc sections (110) is similarly configured but with different preferably tapered thicknesses. The passage-arc-section maximum thickness (210) is preferably about 0.08 to 0.12 millimeters thick near the central opening. The passage-arc-section minimum thickness (211) is preferably about 0.06 to 0.1 millimeters at the periphery. Preferably the minimum space between the bottom of the passage arc sections (110) and the iris at the iridocorneal angle (410) is about 0.04 millimeters.

The annular non-planar structure includes a plurality of auricles (115) extending from the support arc sections (105) and configured to hold the implant (100) in place by engaging the eye (400) at the iridocorneal angle (410). The auricles (115) preferably have a triangular shape when viewed from the top and are to hold or stabilize the implant (100) in a fixed position within the eye (400). Semi-circular or rounded rectangular shapes are alternatives. Each of the auricles (115) is preferably 0.12 to 0.14 millimeters thick and is preferably configured with microscopic holes to make it permeable to fluid flow within the eye (400). The auricles are preferably the same thickness as the support arc sections (105). The base length of the triangle is preferably 0.8 to 1.0 millimeters and its height or distance extended from a circle defining most of the support arc sections (105) is preferably 0.3 to 0.5 millimeters. The auricles (115) are preferably evenly spaced from each other and the passage arc sections (110). The auricles (115) are preferably configured with a rounded end to help minimize damage to structures of the iridocorneal angle (410). The rounded end is one that is not sharp and having an obtuse angle with the support arc section.

When properly configured, the auricles (115) cause almost no stress to angle structures, yet keep the implant in place integrally with its thin, elastic and soft nature. The auricles (115) safely distribute any pressure forces from the ocular tissues over multiple contact points. The auricles (115) should be maximally flexible to keep the implant (100) in the desirable location (immediately above the iris) avoiding any compression that could potentially result above or below the implant. The overall diameter of the implant to the ends of the auricles (115) is preferably between 11.5 to 13.5 millimeters. Thus, the diameter of the circle defining most of the support arc sections (105) is preferably between 10.5 to 12.5 millimeters.

As shown in FIG. 2, each passage arc section (110) is uniformly thinner than each support arc section (105). Also the bottom of the passage arc section (110) is above the bottom of the support arc section (105) in order to form the passage (212).

Figure 5:
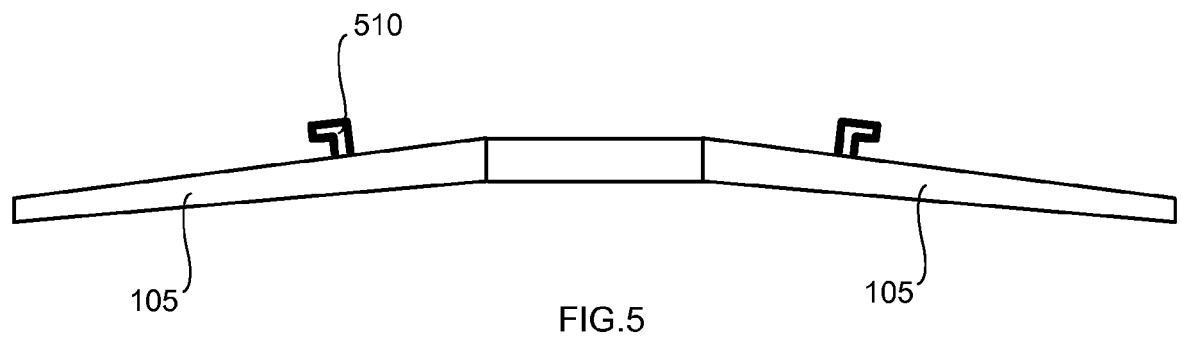
FIG. 5 is a sectional side-elevation view of the ocular implant showing an open-angle-shape spur used to anchor an optional artificial lens to the ocular implant.

FIGS. 5, 7 and 8 illustrate the implant (100) with two versions of an optional spur: FIG. 5 illustrates an outwardly-facing-open-angle-shape spur (510) and FIG. 7 and FIG. 8 illustrate a closed-loop-shape spur (710), which are used to secure an artificial lens that is also an optional addition to the ocular implant. The optional first artificial lens (600) is used with the outwardly-facing-open-angle-shape spur (510) and the optional second artificial lens (700) is used with the closed-loop-shape spur (710). The term "outwardly" refers generally to a direction away from the natural lens (420).

In any of the spur versions, the spur rises from a support arc section (105) away from the iris (405) when implanted in the eye (400) and is configured to provide an anchor point for an artificial lens spanning the natural lens (420) atop the implant (100).

The closed-loop-shape-spur height (811) is preferably in a range of 0.2 to 0.6 millimeters. The closed-loop-shape-spur-opening width (812) is preferably about 0.1 millimeters. The closed-loop-shape-spur-opening height (813) is preferably in a range of about 0.1 to 0.3 millimeters.

FIG. 7 illustrates the implant (100) with the optional second artificial lens (700). This embodiment includes an optional second artificial lens (700), which has as a distinguishing feature a pincer (911) on the second lens haptic foot (901). The first-lens-haptic-foot width (612) is preferably in a range of about 0.35 to 0.75 millimeters and the first-lens-haptic-foot length (613) is preferably in a range of about 0.15 to 0.5 millimeters.

The optional first artificial lens (600) and the optional second artificial lens (700) are refractive components, that is, each is a phakic intraocular lens, typically used to correct high refractive errors, which are not eligible for LASIK (laser-assisted in situ keratomileusis) surgery. An implantable lens is often needed when other vision correction procedures are not a good medical choice, such as when a person has thin corneas or myopia between 3.00 and 20.00 diopters. With some patients receiving phakic intraocular lens, LASIK may be used as a follow-up to refine vision correction.

The artificial refractive lens may also comprise hairclip-like devices (1540), also referred to herein as hairclip devices, or for simplicity, each of the hairclip-like devices may be referred to herein as a hairclip device. The hairclip-like devices (1540) may be needed because the material comprising the implant may be soft and thin and in that form does not easily maintain the vault height (1620) without accessory elements. The hairclip-like devices (1540) are, therefore, preferably made from harder material like PMMA, Poly(m-ethyl methacrylate), which is a clear plastic.

The hairclip-like devices (1540) may be used for implants with and without a refractive lens. The hairclip-like devices (1540) help to minimize the contact surface between iris and the implant by maintaining the vault height (1620). Thus, the hairclip-like devices (1540) are adapted to maintain the vault height (1620) of the implant, and the number and shape of the hairclip-like devices (1540) may vary. FIG. 15A, FIG. 15B, FIG. 15C, and FIG. 15D illustrate a variety of hairclip-like devices (1540).

When used with an implant having an artificial lens, the hairclip-like devices (1540) secure to and engage the implant to support the artificial lens above the surface of the eye. FIG. 17 shows a plan view of a first alternative implant (1700) having a fifth artificial lens (1610) with hairclip devices (1540) that support the fifth artificial lens (1610) above the eye. FIG. 16 shows an elevation view of the fifth artificial lens (1610) where the vault height (1620) of the lens above the surface of the eye is indicated. The space between the hairclip-like devices (1540) and the vault height (1620) allows flow of humour aqoueus so as to minimize risk of pupillary blockage.

When used with an implant having an artificial lens, each hairclip device is a part of the artificial lens that provides the needed structure to lift the artificial lens above the surface of the eye and attach to the main body (1531) of the implant. FIG. 15A is a sectional view of a first hairclip device (1510) for supporting an artificial lens, the first hairclip device (1510) having an end folded down to hold the main body of the implant underneath the hairclip device. FIG. 15B is a sectional view of a second hairclip device (1520) with an end folded up to hold the main body above the second hairclip device (1520). FIG. 15C is a sectional view of a third hairclip device (1530) with an end angled down to wedge the main body underneath the third hairclip device (1530). FIG. 15D is a sectional view of a fourth hairclip device (1540) with a slotted configuration to hold the main body of the implant in the slot.

In any of the embodiments using an artificial lens, the haptic is configured to engage the spur to hold the artificial lens in position and to elevate the artificial lens off the top surface of the implant and the iris. This is illustrated in FIG. 10, which is a side elevation view of a portion of the optional second artificial lens (700) atop a portion of the support arc section (105). The second-lens-haptic thickness (1011) is preferably in a range of 0.1 to 0.3 millimeters. The second-lens-haptic-foot length (1013) is preferably in a range of 0.15 to 0.5 millimeters. The second-lens-haptic-rise distance (1012) is preferably in a range of 0.25 to 0.5 millimeters. The second-lens-haptic-frame distance (1014) is preferably about 0.5 millimeters. The second-lens-haptic height (1015) is preferably in a range of 0.25 to 0.5 millimeters.

Figure 6:
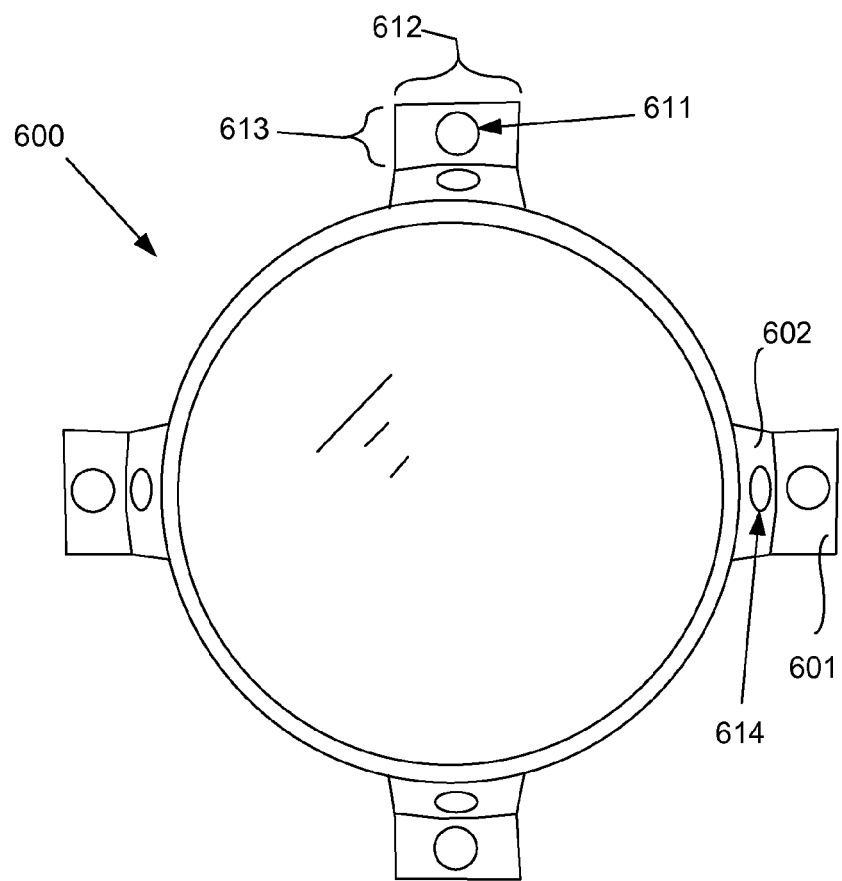
FIG. 6 is a first-lens haptic with closed-hole to secure to the spur shown in FIG. 5.

Preferably, there are four haptics, evenly spaced from each other, as shown in FIGS. 6 and 9. The diameter of the refractive part is greater than the diameter of the central opening of the non-refractive part. Both the non-refractive part and any optional artificial lens are also foldable, biocompatible materials. It is noted that the number and thickness of the arc sections may vary to suit the application, for example with or without an artificial lens.

In the example lenses shown in FIGS. 6 and 9, the haptic comprises a riser to elevate the artificial lens: namely the first-lens haptic riser (602) elevates the optional first artificial lens (600); and a second-lens haptic riser (902) elevates the optional second artificial lens (700). The riser is configured to define a hole to enable free flow of humour aqueous under the artificial lens. For the optional first artificial lens (600), this hole (614) is shown in the first-lens haptic riser (602). For the optional second artificial lens (700), this hole (914) is shown in the second-lens haptic riser (902).

Since the implant (100) is flexible, it is readily folded and inserted into the eye through a peripheral corneal surgical incision about 3.5 millimeters long. The cornea need not be sutured for this incision length. This is a very simple, short, safe and painless procedure. When an optional first artificial lens (600) is used, after placing the non-refractive part properly in the anterior chamber (415), the refractive part is inserted through the same incision, since it is also foldable. Then, each of the four haptics in a preferred embodiment is then engaged on the spur rising from the support-arc-section top-surface (220).

Figure 11:
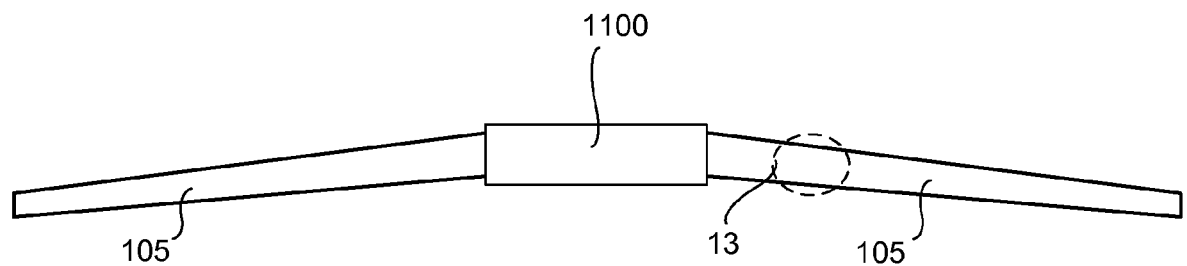
FIG. 11 is a sectional side elevation view of an ocular implant with a third artificial lens.
Figure 12:
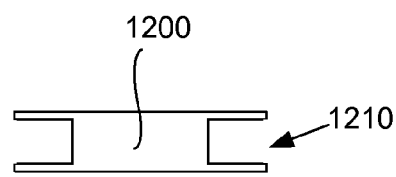
FIG. 12 is a side elevation view of a fourth artificial lens.

The additional refractive part, also referred to as the artificial lens, is preferably placed at the level of the center of the main non-refractive body, also referred to as the implant (100). So the combination of artificial lens and implant (100) will allow the surgeon to insert the unit easily. The surgeon will not have to deal with attaching the refractive part, namely the artificial lens, after he/she inserts the main non-refractive color part, namely the implant (100). When main body, namely the implant (100) is placed properly, the refractive part will be placed at the same time. These versions are illustrated in FIG. 11 and FIG. 12. Of course, the refractive part (artificial lens) is preferably clear in all versions and not colored. The microscopic holes (1310), or pores, on the passage arc sections in combination with the flow under the passage arc sections, will more enable maximal natural aqueous humor flow.

FIG. 11 is a sectional side elevation view of an ocular implant with a third artificial lens (1100). This is a monoblock combination ocular implant and artificial lens that does not employ spurs to affix the artificial lens. The refractive part, that is namely the third artificial lens (1100), is at the level of the central opening, not above or below it.

FIG. 12 is a side elevation view of a fourth artificial lens (1200) configured with a slot (1210) to receive the ocular implant. This embodiment with a non-refractive part and a refractive lens does not include spurs.

For any of the embodiments employing an artificial lens the ocular implant is configured to cover the natural lens when the implant is implanted in the eye atop the iris.

FIG. 18 is a plan view of a second alternative implant (1800) having a sixth artificial lens (1830). The sixth artificial lens (1830) is preferably about 3.0 millimeters to about 6.0 millimeters in diameter. FIG. 18 further shows drainage holes (1840) in the alternative main body (1820) of the second alternative implant (1800). The drainage holes (1840) are preferably microscopic in diameter and invisible to the human eye.

The sixth artificial lens (1830) also shown in FIG. 20, has protrusions (2010). FIG. 20 also shows the mating holes (2020) for the protrusions (2010). The mating holes (2020) for the protrusions (2010) are in the alternative main body (1820) of the second alternative implant (1800). FIG. 18 identifies the protrusions/mating holes which in the plan view are represented by the round dot (1850). The protrusions extend from the artificial lens, wherein the main body (1820) is configured to define a plurality of attachment holes to mate with the protrusions and affix the artificial lens to the material.

All embodiments of the implant (100) may utilize a peripheric ring (1710), also known as a limbal ring. The peripheric ring (1710) is preferably a small black ring that surrounds the iris of the ocular implant. The peripheric ring (1710) is preferably up to about 2 millimeters in width, which surrounds the iris to define an outer edge to the iris.

FIG. 19 is a plan view of a third artificial implant with a peripheric ring (1710) and seventh artificial refractive lens (1910). The peripheric ring (1710) may be placed in the anterior chamber (415) of a person's eye. The peripheric ring (1710) preferably includes support arc sections (105) and passage arc sections (110) to enable fluid flow. These should be mated up with the corresponding support arc sections (105) and passage arc sections (110) on the main body (1531).

The peripheric ring (1710) may also be made of a permeable material to enable fluid flow through them. In alternative embodiments, a similar ring around the pupil may be used and this pupil ring may be a refractive lens.

In further alternative embodiments, the peripheric ring (1710) may be implanted under the conjunctiva. The conjunctiva is a transparent membrane that lies over the tenon and sclera. A preferable limbal ring is placed easily under the conjunctiva with topical anesthesia. The peripheric ring (1710) may be made of retinal cerclage material because such material is expected to have little or no side effects. When you place a inert material (like retinal cerclage procedure) under the conjunctiva, it is safe, non-inflammatory and permanent. This type of implant is expected to be of similar risk as a contact lens, which is used to make the eye look bigger.

Implantation under the conjunctiva is preferable because this surgical procedure rarely results in glaucoma, intraocular inflammation, and other side effects. An implant under the conjunctiva is preferable because a limbal ring not having contact with the iris will eliminate risk of inflammation, high ocular pressure, and will not disturb pupil dilation. This translates to very low risk of corneal damage, such as for example, edema, endothelial cell loss, intraocular inflammation, pigment cell dispersion in the anterior chamber, glaucoma, cataract and even light sensitivity.

The peripheric ring (1710) may be any desired width or color desired by the person using the implant. It may be used to make the natural iris color stand out. Color variations are known to make the iris appear larger. This is something like a contact lens which is permanent and safe FIG. 21 is an elevation view of an implant with a glued artificial lens (2110), that is, it is attached to the ocular implant using an adhesive. A drainage hole (1840) is shown in the second alternative main body (2120).

FIG. 22 is a plan view of an alternative peripheric ring (2200) with a pin connector (2210). Circular enclosure (23) identifies for magnification purposes a portion of the peripheric ring (2200) with the pin connector (2210). Circular enclosure (23) represents the enlarged views in FIG. 23A and FIG. 23B. Two versions of the pin connector (2210) are shown. A short pin connector (2310) mates two overlapping ends of the peripheric ring (2200) together in tight joint. A long pin connector (2320) mates the two ends with a separated connection having space between the overlapping ends to permit fluid flow.

FIG. 23A is a plan view of showing a magnified portion of the peripheric ring with sealed pin joint.

FIG. 23B is a plan view of showing a magnified portion of the peripheric ring with separated pin joint.

The implant (100) can be made to accommodate any iris design and any pupil opening desired. For example, it may have a wider pupil opening to show full pupil dilation. An implant (100) will typically be printed with pigment color to match iris patterns and blend in with a person's natural eye color, for example brown with specs of black. Different shapes, letters, signs etc. may also be printed on the implant. A wider pupil opening also permits more aqueous flow, and less contact with the iris.

Also the implant (100) may have other openings on any part of the implant (100) that would be part of the implant design to allow brown specs of natural iris to be shown and blend in with the print design on the implant (100). Such openings also improve aqueous flow through the implant (100). The paint pigment on the implant (100) may be transparent to allow the natural iris to show through. The implant (100) may also have streaks of brown to make different designs using natural eye color behind implant (100).

Figure 24:
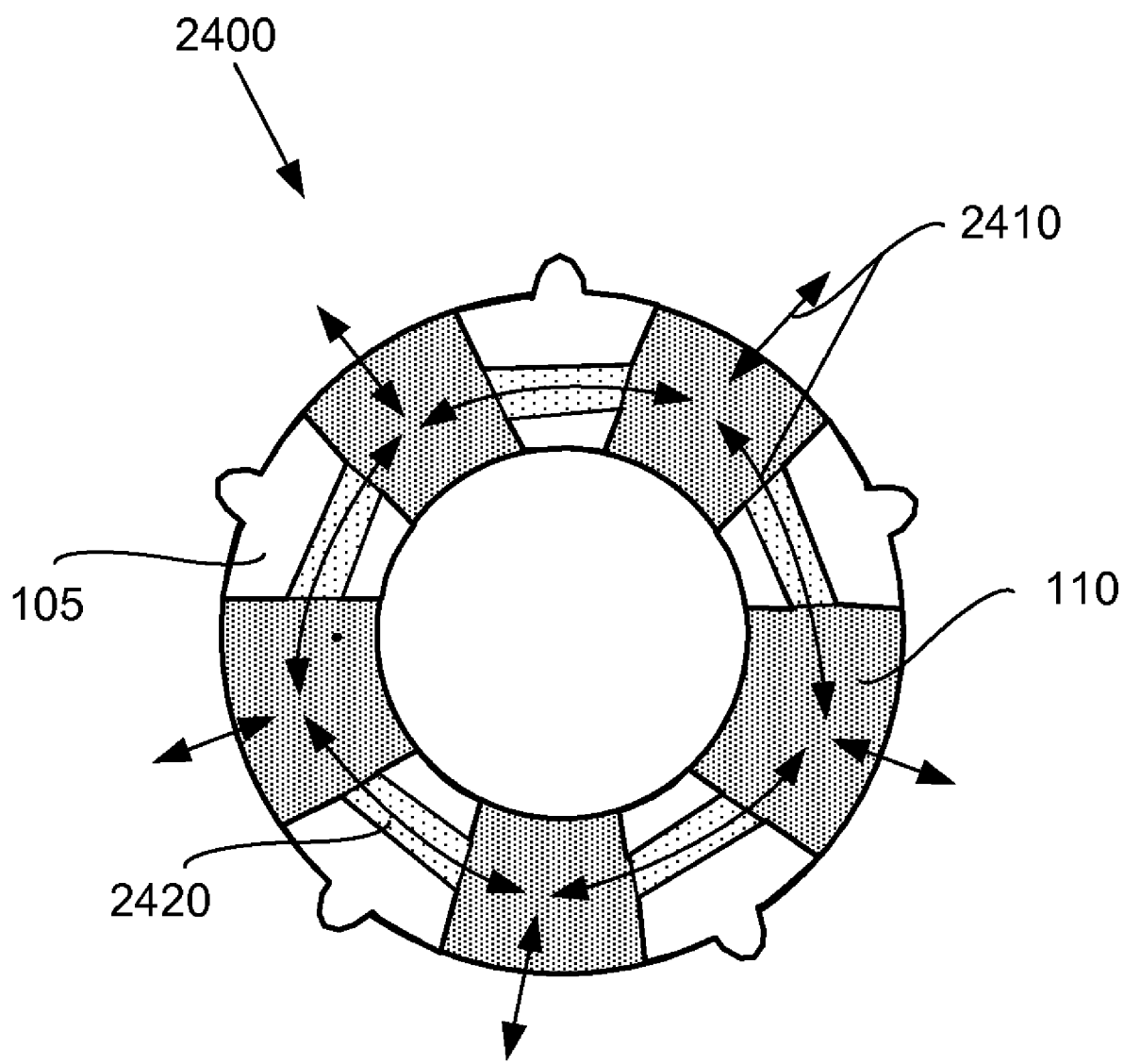
FIG. 24 is a plan view an implant showing grooves through support arc sections.

FIG. 24 illustrates a third alternative implant (2400) with grooves (2420), essentially circumferential grooves, through the support arc section (105). A support arc section (105) is thus configured to define a groove across the support arc section (105). Double-headed arrows (2410) indicate aqueous flow directions. Each of the grooves (2420) across a support arc section (105) enables aqueous flow across the support arc section. Additional grooves translate to have less contact with iris and less chance inflammation and increased ocular pressure. The third alternative embodiment (2400) illustrates the concept that the implant includes variations having grooves and hairclip devices or ribs in different numbers, sizes, thicknesses, different directions variations, even grooves on the hairclip devices.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the medical industry.

What is claimed is:

1. An implant for an eye, the eye comprising an anterior chamber, an iridocorneal angle, a natural lens, and an iris, the implant configured to extend over the iris within the anterior chamber to alter iris color for medical and cosmetic purposes, the implant comprising:
    a material that is inert, nontoxic and foldable, the material configured to define an annular non-planar structure, with a central opening and a periphery;
    the annular non-planar structure configured to leave the natural lens uncovered and further configured to extend approximately to the iridocorneal angle when implanted in the eye atop the iris;
    the annular non-planar structure comprising a plurality of arc sections, the arc sections comprising support arc sections of a non-uniform thickness that diminishes from the central opening to the periphery and passage arc sections, wherein each arc section comprises a top surface and a bottom surface,
    the arc sections configured, when implanted in the eye atop the iris, to define:
        passages for humor aqueous flow under the implant formed by passage arc sections that sit a distance above the iris; and,
        a support structure for the passages formed by support arc sections that are in contact with the iris;
    auricles extending from the support arc sections and configured to hold the implant in place by engaging the eye at the iridocorneal angle;
    an artificial lens configured to cover the natural lens when the implant is in the eye atop the iris.

2. The implant of claim 1, further comprising protrusions extending from the artificial lens, wherein the material is configured to define a plurality of attachment holes to mate with the protrusions and affix the artificial lens to the material.

3. The implant of claim 1, wherein the artificial lens is configured to define a plurality of drainage holes to render the artificial lens permeable to fluid within the eye.

4. An implant for an eye, the eye comprising an anterior chamber, an iridocorneal angle, a natural lens, and an iris, the implant configured to extend over the iris within the anterior chamber to alter iris color for medical and cosmetic purposes, the implant comprising:
    a material that is inert, nontoxic and foldable, the material configured to define an annular non-planar structure, with a central opening and a periphery;
    the annular non-planar structure configured to leave the natural lens uncovered and further configured to extend approximately to the iridocorneal angle when implanted in the eye atop the iris;
    the annular non-planar structure comprising a plurality of arc sections of a non-uniform thickness, the arc sections comprising support arc sections of a non-uniform thickness that diminishes from the central opening to the periphery and passage arc sections, wherein each arc section comprises a top surface and a bottom surface,
    the arc sections configured, when implanted in the eye atop the iris, to define:
        passages for humor aqueous flow under the implant formed by passage arc sections that sit a distance above the iris; and,
        a support structure for the passages formed by support arc sections that are in contact with the iris;
    auricles extending from the support arc sections and configured to hold the implant in place by engaging the eye at the iridocorneal angle; and
    a peripheric ring up to about 2 millimeters in width that surrounds the iris to define an outer edge to the iris.

5. The implant of claim 4, wherein the eye comprises a conjunctiva and the peripheric ring is implanted under the conjunctiva.

6. An implant for an eye, the eye comprising an anterior chamber, an iridocorneal angle, a natural lens, and an iris, the implant configured to extend over the iris within the anterior chamber to alter iris color for medical and cosmetic purposes, the implant comprising:
    a material that is inert, nontoxic and foldable, the material configured to define an annular non-planar structure, with a central opening and a periphery;
    the annular non-planar structure configured to leave the natural lens uncovered and further configured to extend approximately to the iridocorneal angle when implanted in the eye atop the iris;
    the annular non-planar structure comprising a plurality of arc sections of a non-uniform thickness, the arc sections comprising support arc sections of a non-uniform thickness that diminishes from the central opening to the periphery and passage arc sections, wherein each arc section comprises a top surface and a bottom surface,
    the arc sections configured, when implanted in the eye atop the iris, to define:
        passages for humor aqueous flow under the implant formed by passage arc sections that sit a distance above the iris; and
        a support structure for the passages formed by support arc sections that are in contact with the iris;
    auricles extending from the support arc sections and configured to hold the implant in place by engaging the eye at the iridocorneal angle; and
    wherein at least one of the support arc sections is configured to define a groove across said support arc section.

* * * * *